(12) United States Patent
Heidebach et al.

(10) Patent No.: US 9,795,154 B2
(45) Date of Patent: Oct. 24, 2017

(54) ENZYMATIC TREATMENT OF GUM ARABIC

(71) Applicant: Rudolf Wild GmbH & Co. KG, Eppelheim (DE)

(72) Inventors: Thomas Heidebach, Heidelberg (DE); Matthias Sass, Oftersheim (DE); Axel De With, Plankstadt (DE)

(73) Assignee: RUDOLF WILD GMBH & CO. KG, Eppelheim (DE)

( * ) Notice: Subject to any disclaimer, the term of this patent is extended or adjusted under 35 U.S.C. 154(b) by 198 days.

(21) Appl. No.: 14/358,044

(22) PCT Filed: Dec. 12, 2012

(86) PCT No.: PCT/EP2012/005129
§ 371 (c)(1),
(2) Date: May 14, 2014

(87) PCT Pub. No.: WO2013/091799
PCT Pub. Date: Jun. 27, 2013

(65) Prior Publication Data
US 2014/0302197 A1    Oct. 9, 2014

(30) Foreign Application Priority Data

Dec. 22, 2011 (EP) .................... 11010090

(51) Int. Cl.
*A23L 1/053* (2006.01)
*A23L 2/52* (2006.01)
(Continued)

(52) U.S. Cl.
CPC ............... *A23L 1/053* (2013.01); *A23L 2/52* (2013.01); *A23L 29/25* (2016.08); *C12P 19/02* (2013.01); *C12P 19/14* (2013.01)

(58) Field of Classification Search
CPC ............................ A23L 1/053; A23K 1/1606
(Continued)

(56) References Cited

U.S. PATENT DOCUMENTS 4,479,971 A    10/1984  Eng et al.
2005/0124805 A1*  6/2005  Al-Assaf ............... A23L 1/0029
                                           536/27.4
(Continued)

FOREIGN PATENT DOCUMENTS

WO    2005042788 A1    5/2005
WO    2008112966 A1    9/2008

OTHER PUBLICATIONS

International Search Report issued in corresponding International Patent Application No. PCT/EP2012/005129 dated Jan. 23, 2013 (3 pages).

(Continued)

*Primary Examiner* — Helen F Heggestad
(74) *Attorney, Agent, or Firm* — Kilyk & Bowersox, P.L.L.C.

(57) ABSTRACT

The present invention relates to a method for preparing modified gum arabic comprising treating gum arabic with an enzyme selected from the group of glycosidases at a concentration of 1 to 1000 units of enzyme per gram of gum arabic, a modified gum arabic obtainable by said method, an emulsion comprising the modified gum arabic and a beverage concentrate and ready-to-drink beverage comprising the emulsion.

10 Claims, 7 Drawing Sheets

Time-dependent release of galactose during enzymatic treatment of 20% gum arabic solution at 50°C with different lactase concentrations.

(51) Int. Cl.
*C12P 19/02* (2006.01)
*C12P 19/14* (2006.01)
*A23L 29/25* (2016.01)

(58) Field of Classification Search
USPC .................................. 426/10, 573, 590, 601
See application file for complete search history.

(56) References Cited

U.S. PATENT DOCUMENTS

2008/0124437 A1    5/2008  Fang et al.
2009/0010861 A1*   1/2009  Beck ................... A23K 1/1606
                                                            424/59

OTHER PUBLICATIONS

Chikamai et al., "Processing of Gum Arabic and Some New Opportunities", Food Hydrocolloids, vol. 10, No. 3, 1996, pp. 309-316.

* cited by examiner

Fig. 1: Time-dependent release of galactose during enzymatic treatment of 20% gum arabic solution at 50°C with different lactase concentrations.
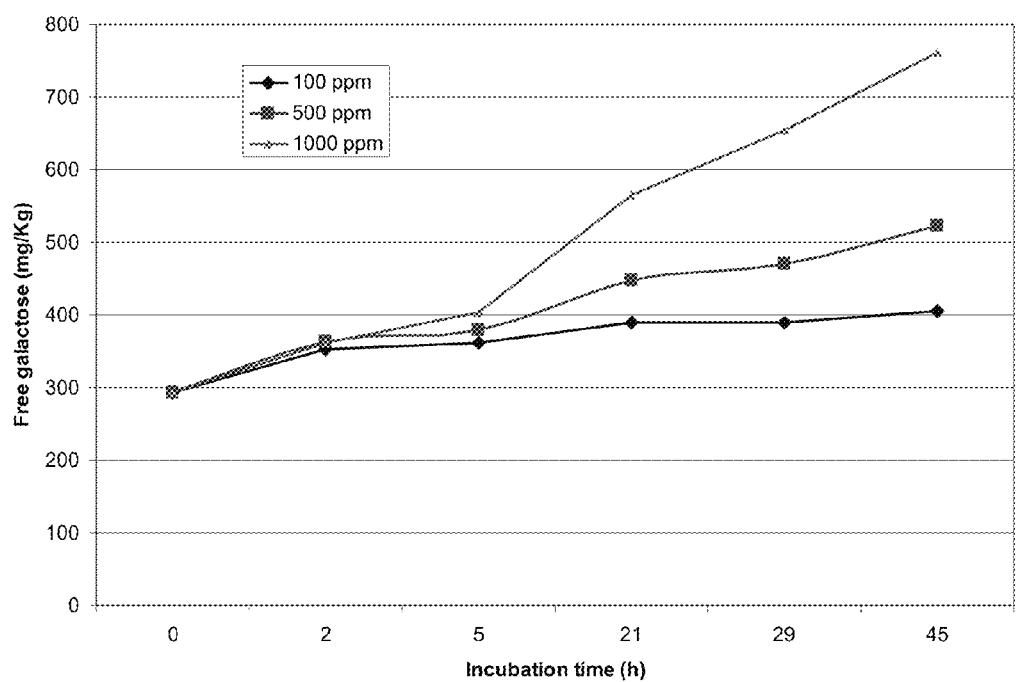

Fig. 2a: HPLC-UV chromatogram of the gum arabic solution before enzymatic treatment
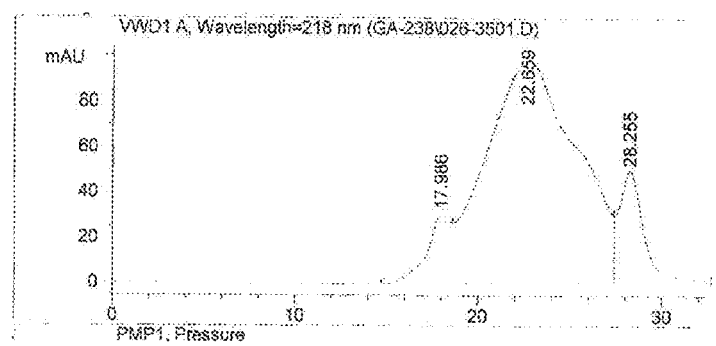
Fig. 2b: HPLC-UV chromatogram of the gum arabic solution after enzymatic treatment (100 ppm/ 45 h/50°C)
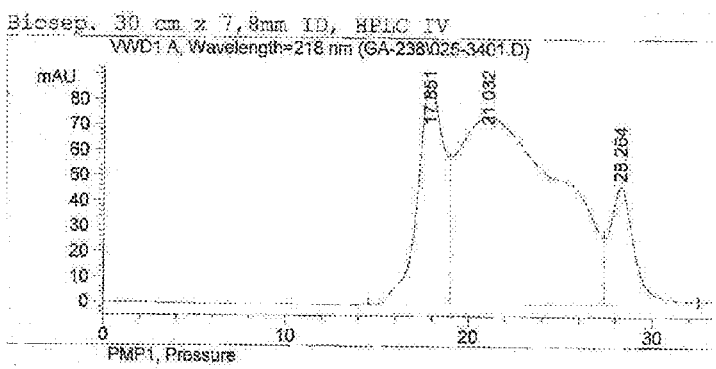

Fig. 3a: Particle size ($X_{90,3}$; μm) of the emulsions with and without enzymatic treatment
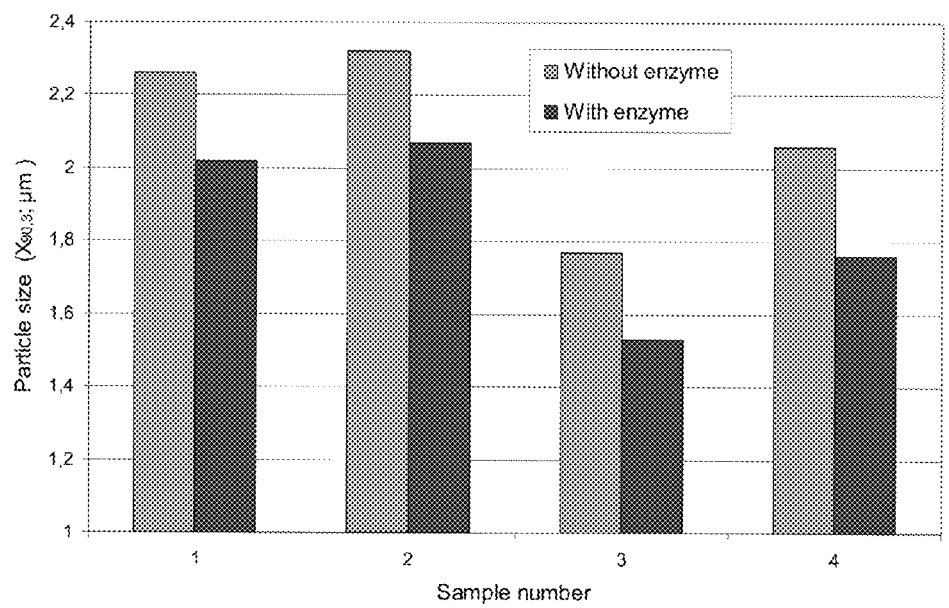
Fig. 3b: Increase in particle size ($X_{90,3}$; μm) of the emulsions, due to heat treatment (90°C/20 min)
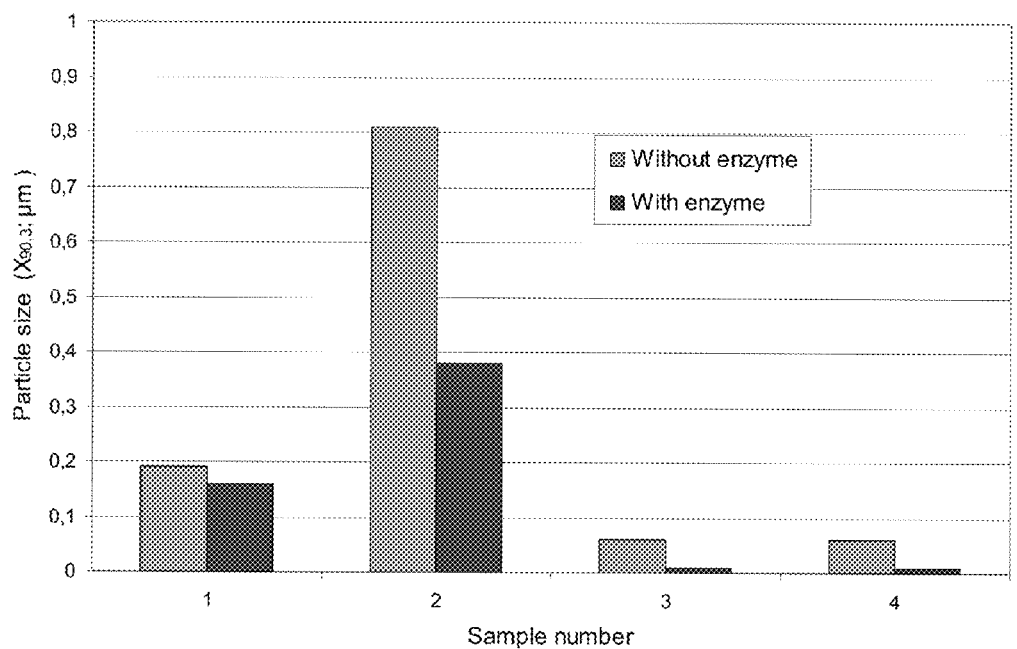

Fig. 4a: Particle size ($X_{90,3}$; μm) of emulsions prepared from differently treated gum arabic solutions, each incubated at 45°C for 40 h.
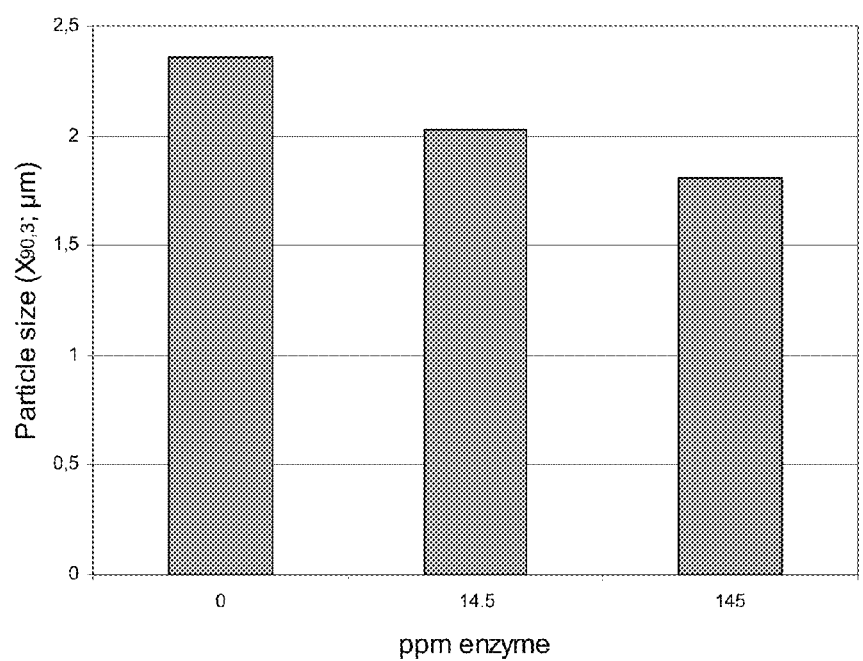

Fig. 4b: Particle size ($X_{90,3}$; μm) from emulsions prepared from differently treated gum arabic solutions, each incubated with 145 ppm for 40 h.
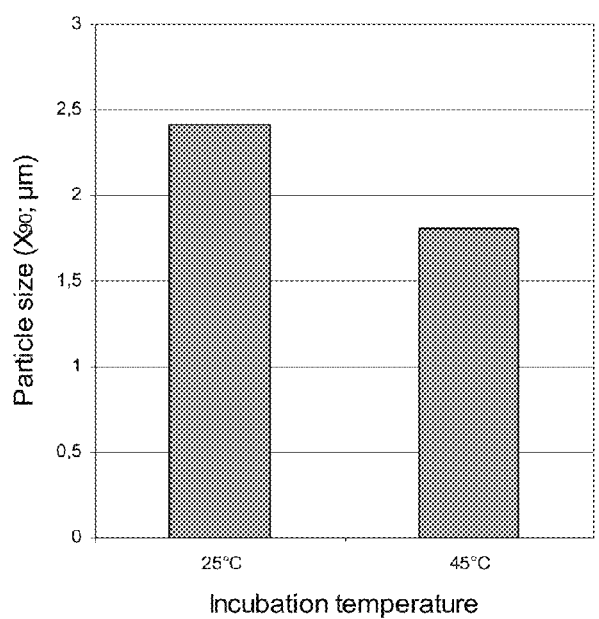

Fig. 5: Particle size ($X_{90.3}$; μm) of the emulsions with and without enzymatic treatment directly after emulsion production and after 20 min heating at 90°C.
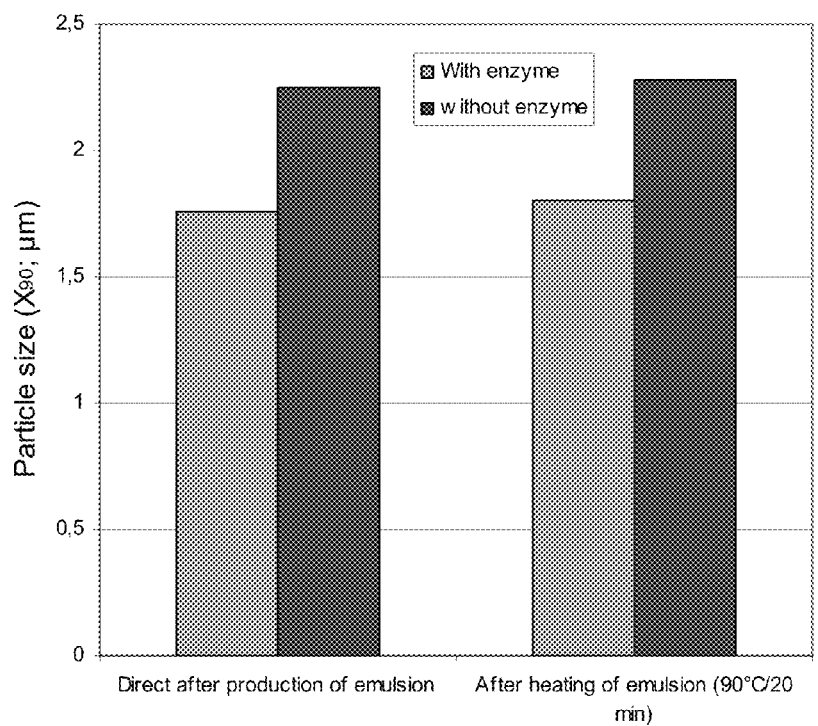

Fig. 6: Particle size ($X_{90,3}$; μm) of the emulsions with and without enzymatic treatment directly after emulsion production by means of high-pressure homogenizer and after 20 min heating at 90°C.
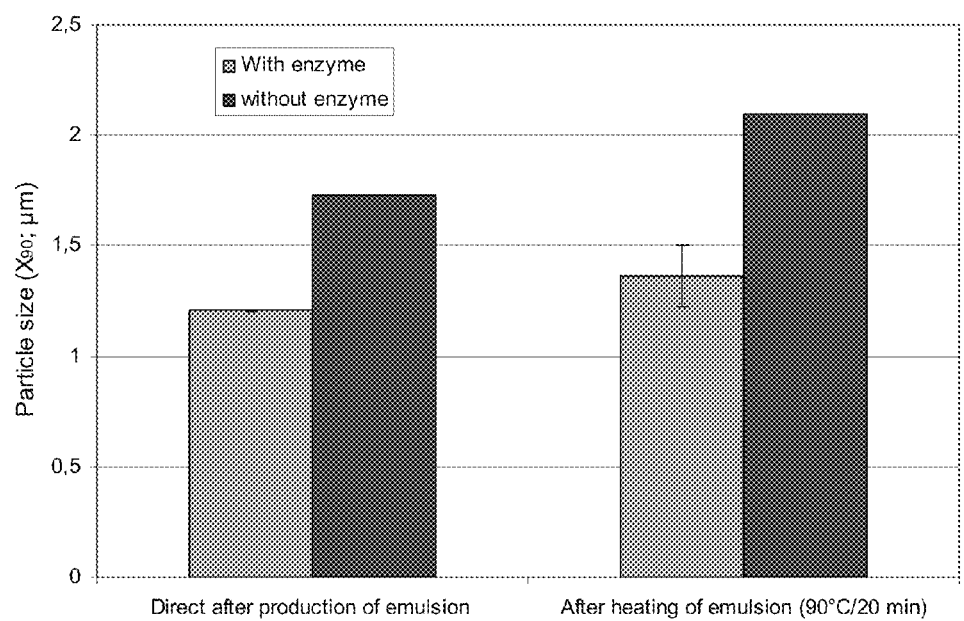

ENZYMATIC TREATMENT OF GUM ARABIC

This application is a National Stage Application of PCT/EP2012/005129, filed Dec. 12, 2012, which claims priority to European Patent Application No. 11010090.6, filed Dec. 22, 2011.

The present invention relates to a method for modifying gum arabic in order to increase its emulsifying properties.

Gum arabic, also known as acacia gum, chaar gund, char goond, or meska, is a natural plant exudate which is considered as the oldest and best known of the gums. It is commercially harvested from wild trees throughout the Sahel, in particular in Senegal, Sudan and Somalia.

Gum arabic is a mixture of polysaccharides and glycoproteins and is primarily used in the food industry as a stabilizer. Gum arabic further acts as an emulsion former and shows excellent acid stability, high solubility in water, low viscosity at high concentrations, as well as adhesive and binding properties. Because of its suitable functional properties and good availability, and since it is moreover edible, it is mostly used in food applications as a functional ingredient, for example as an emulsifier, flavouring agent, humectant, thickener, or surface-finishing agent in confectionery, beverages, emulsions, flavour encapsulation, bakery products and brewing.

Besides its application in food, gum arabic is further used in pharmaceuticals, printing, paint production, glue, and cosmetics as well as in various industrial applications, including viscosity control in inks and in textile industries.

Gum arabic as a natural product is provided by trees of the species *Acacia*. *Acacia senegal*, *Acacia seyal* and *Acacia polyacantha* have the widest distribution among the gum arabic producing trees. While the subspecies *Acacia Senegal* var. *senegal* is by far the one of most commercial relevance, relatively small amounts of gum arabic are produced from *Acacia senegal* var. *kerensis* and *Acacia seyal*.

For the production of commercial gum arabic, the raw exudate is harvested in the form of large (5 cm diameter) nodules or tears. Mature trees, 4.5 to 6 m high and 5 to 25 years old, are tapped by making incisions in the branches and stripping away bark to accelerate exudation. The gum dries into rough spheres which are manually collected and subsequently classified in different qualities. The native gum arabic pieces are crushed to granulate, dissolved in water, filtered, pasteurized and dried, mostly by spray-drying. These powders are standardized within a certain range, provided by different suppliers and sold as food-additive E 414.

From a structural point of view, gum arabic represents a complex mixture of heteropolysaccharides consisting of mainly high molecular mass polysaccharides composed of arabinose, galactose, rhamnose and glucuronic acid. It also contains small amounts of glycoproteins as an integral part of the structure. With its amphiphilic character, gum arabic shows high surface activity, associated with good emulsifying properties. It readily dissolves in water up to high concentrations without substantially increasing the viscosity. It is believed that the more hydropohobic polypeptide chain is adsorbed at the oil-water interface, while the highly branched hydrophilic carbohydrate blocks protrude into the aqueous phase, thus providing a strong sterical hindrance (Islam, A. M., Philips, G. O., Sljivo, A., Snowden, M. J., Williams, P. A. *Food Hydrocolloids,* 1997, 11, 493-505). Although not fully understood, it is suggested that for a satisfying emulsifying activity also the presence of minor, relatively protein rich components is required, since treatment of gum arabic with proteolytic enzymes leads to a loss in the emulsifying capacity (Yadav, M. P.; Igartuburu, J. M.; Yan, Y.; Nothnagel, E. A., *Food Hydrocolloids,* 2007, 21, 297-308).

Several patents describe the modification of gum arabic to enhance its functional emulsifying properties. EP-A-1505078 is directed to a process for modifying gum arabic by means of heating the gum arabic at a temperature higher than 40° C. in humid conditions, which enhances its emulsifying ability.

Similarly, EP-A-1666502 discloses a heat treatment of gum arabic, albeit under dry conditions, leading to an improvement of its emulsifying ability.

EP-A-1734056 relates to a process for the modification of gum arabic by dissolving gum arabic in water and then heat-treating the solution at a temperature below 60° C., thus improving its emulsification properties.

US-A-2005/124805 also discloses modified gum arabic (from *Acacia senegal* or *Acacia seyal*), which has improved emulsifying ability. The modified gum arabic is obtained by heating the gum arabic at 110° C. for not less than 10 hours.

In all above-mentioned patents, a physical treatment of gum arabic is used for achieving remarkably higher emulsifying abilities, expressed in the form of smaller oil droplet diameters in gum arabic stabilized oil-in-water emulsions. However, none of the above documents relate to an enzymatic treatment of gum arabic.

A different strategy known in the art for the treatment of gum arabic consists in the application of enzymes, which modify the polysaccharide structure of gum arabic by cleaving glycosidic bonds. This hydrolysis reaction can be performed with so-called glycosidases (classified by the EC number 3.2.1.X, and synonymously called "glycoside hydrolases" or "glycosyl hydrolases") that are able to catalyze the hydrolytic cleavage of the glycosidic linkage to release smaller sugars from gum arabic.

β-Galactosidase (β-D-galactoside galactohydrolase, EC 3.2.1.23), for example, is a glycoside hydrolase that catalyzes the hydrolysis of the terminal non-reducing β-D-galactose residues in β-D-galactosides. Commercial β-galactosidase is often known and sold as "lactase", since it is capable to hydrolyse lactose into galactose and glucose in bovine milk. In this context, commercial lactase preparations are widely used for the preparation of lactose-free versions of various kinds of commercial dairy products, as well as digestive aids. Because of the high selectivity of the reaction, no other fields of application besides hydrolysis of lactose are currently suggested for commercial lactase preparations (Handbook of Food Enzymology, Editors Whitaker, J. R., Voragen, A. G. J., Wong, D. W. S., Marcel Dekker, New York, 2002, Chapter 65, β-Galactosidase).

Further enzymes selected from the group of glycosidases are arabinogalactan endo-1,4-β-galactosidase (EC 3.2.1.89), arabinan endo-1,5-α-L-arabinosidase (EC 3.2.1.99), mannan endo-1,4-β-mannosidase (EC 3.2.1.78), xylan 1,4-β-xylosidase (EC 3.2.1.37), endo-1,4-β-xylanase (EC 3.2.1.8), α-N-arabinofuranosidase (EC 3.2.1.55), glucuronoarabinoxylan endo-1,4-β-xylanase (EC 3.2.1.136) and β-glucuronidase (EC 3.2.1.31).

WO-A-2005/042788 is directed to a process for separating and recovering arabinose and other monosaccarides from gum arabic by means of controlled enzymatic hydrolysis which is achieved with enzymes such as arabinofuranosidases and xylanases. However, the document does not relate to the modification of the emulsifying properties of gum arabic.

Chikamai (Chikamai, E. N. B., *The availability, quality and processing aspects of gum Arabic from Kenya*, Dissertation, 1994, University of Wales) treated aqueous solutions of gum arabic (*Acacia senegal* var. *kerensis*) with a highly purified β-galactosidase (G3522, purchased from Sigma). This study was designed to investigate ways of reducing viscosity and gelling of gum arabic solutions without drastically affecting its emulsification functional properties. In this context, experiments on enzyme hydrolysis of the gum arabic molecule were conducted. While the viscosity decreased significantly due to enzymatic hydrolysis, the emulsifying properties remained unchanged. Furthermore, the authors found a significant increase in the relative protein content of the remaining gum arabic molecules due to a highly selective hydrolysis of a substantial amount of galactose (~8%) caused by the enzymatic treatment.

In contrast to the above study, it has been surprisingly found in connection with the present invention that treatment of gum arabic from various sources with commercial enzymes selected from the group of glycosidases can significantly increase its emulsifying properties. Such an improvement due to enzymatic treatment of gum arabic was observed for emulsions prepared from both native, untreated gum arabic, and processed and dried powder samples of gum arabic.

Pursuant to the present invention, commercially available enzymes selected from the group of glycosidases can be readily used to modify gum arabic by controlled hydrolysis of the gum arabic molecule. When using β-galactosidase as enzyme, it has been further found that only very small amounts of galactose (0.01 to 0.3% based on applied gum arabic mass) must be removed from the gum arabic molecule so as to achieve a significant effect on emulsion improvement.

Therefore, it is the object of the present invention to provide modified gum arabic having improved emulsifying properties. Said object is solved by a method for preparing modified gum arabic comprising treating gum arabic with an enzyme selected from the group of glycosidases at a concentration of 1 to 1000 units of enzyme per gram of gum arabic.

Said object is also solved by a modified gum arabic, which is obtainable by the method according to the invention.

The gum arabic for enzymatic treatment according to the present invention is usually derived from an exudate from the stems and branches of sub-Saharan *Acadia senegal*, *Acacia seyal* or *Acacia polyacantha* trees. In a preferred embodiment, in combination with any of the embodiments listed below or above, the gum arabic is derived from *Acadia senegal*, in a more preferred embodiment, in combination with any of the embodiments listed below or above, the gum arabic is derived from *Acacia senegal* var. *senegal*, *Acacia senegal* var. *kerensis*, and *Acacia senegal* var. *rostata*, and in a particularly preferred embodiment, in combination with any of the embodiments listed below or above, the gum arabic is derived from *Acacia senegal* var. *Senegal*.

The enzyme treatment of gum arabic according to the invention can be carried out with native, raw and unprocessed gum arabic that has merely been crushed into granules upon harvest from the tree. In a preferred embodiment, in combination with any of the embodiments listed below or above, the gum arabic is further processed and purified before enzymatic treatment according to the invention. The processing and purification of gum arabic upon harvest comprises the steps of crushing the raw, hard gum arabic into pieces, dissolving them in water, filtering the resulting solution, pasteurizing and finally drying. The drying is preferably conducted as spray-drying. The so processed gum arabic is obtained as a powder, which can be commercially purchased.

The term "unit" as used in the present invention is defined as the quantity of enzyme that will liberate one μmole of o-nitrophenol per minute from a o-nitrophenyl-β-D-galactopyranoside substrate under assay conditions, according to the Food Chemicals Codex Compendium (Second supplement of the Third Edition, 1981, National Academic Press, Washington D.C., USA).

The enzyme for the treatment of gum arabic according to the method of the invention is selected from the group of glycosidases. In a preferred embodiment of the invention, in combination with any of the embodiments listed above or below, the enzyme is selected from β-galactosidase (EC 3.2.1.23), arabinogalactan endo-1,4-β-galactosidase (EC 3.2.1.89), arabinan endo-1,5-α-L-arabinosidase (EC 3.2.1.99), mannan endo-1,4-β-mannosidase (EC 3.2.1.78), xylan 1,4-β-xylosidase (EC 3.2.1.37), endo-1,4-β-xylanase (EC 3.2.1.8), α-N-arabinofuranosidase (EC 3.2.1.55), glucuronoarabinoxylan endo-1,4-β-xylanase (EC 3.2.1.136) and β-glucuronidase (EC 3.2.1.31). In a particularly preferred embodiment, in combination with any of the embodiments listed above or below, the enzyme is β-galactosidase.

The β-galactosidase according to the invention represents a glycoside hydrolase which comprises all enzymes, hydrolases, compounds, substances, materials, compositions and preparations that are identified by the EC number 3.2.1.23. The term "β-galactosidase" and the term "lactase" are used synonymously herein.

The enzymes selected from the group of glycosidases for the treatment of gum arabic in accordance with the present invention can be purchased from different commercial sources. Accordingly, glycosidase samples from different suppliers might vary in their specific composition, activity and purity in terms of side-activities from other enzymes. In a preferred embodiment, in combination with any of the embodiments listed below or above, the purity of the enzyme (with respect to the presence of other enzyme impurities) is higher than 90%. In a more preferred embodiment, in combination with any of the embodiments listed below or above, the purity of the enzyme is higher than 95%. In a particularly preferred embodiment, in combination with any of the embodiments listed below or above, the purity of the enzyme is higher than 98%.

In the method in accordance with the present invention, gum arabic is treated with an enzyme selected from the group of glycosidases. Gum arabic is dissolved in water and the enzyme is added. In a preferred embodiment, in combination with any of the embodiments listed above and below, in the method according to the invention the concentration of the enzyme per gram of gum arabic is 10 to 500 units. In a more preferred embodiment, in combination with any of the embodiments listed above and below, the concentration of the enzyme per gram of gum arabic in the method according to the invention is 20 to 350 units, in particular 28 to 280 units.

Temperature and pH-value of the enzymatic treatment according to the invention is chosen to achieve maximum reaction speed of the process. Such an optimum can generally vary for different commercial enzyme preparations. In a preferred embodiment of the invention, in combination with any of the embodiments listed above and below, the gum arabic is treated with the enzyme at a temperature of 0 to 70° C. In a more preferred embodiment of the invention, in combination with any of the embodiments listed above and below, the treatment of gum arabic with the enzyme according to the invention is performed at temperatures of 40 to 60° C., in particular at 50° C.

For reasons of microbiological contamination, an enzyme preparation with a maximum activity and lowest optimum incubation temperature is preferred, to keep the required process duration as short as possible at a lowest possible temperature. Therefore, it is another preferred embodiment of the invention, in combination with any of the embodiments listed above and below, to perform the enzymatic treatment of gum arabic according to the invention at temperatures of 0 to 15° C.

In a further preferred embodiment of the invention, in combination with any of the embodiments listed above and below, the gum arabic is treated as a solution with a dry matter content of 5 to 60 wt % based on the total weight of the solution. In a more preferred embodiment of the invention, in combination with any of the embodiments listed below or above, the dry matter content of gum arabic in the solution in accordance with the invention is 20 to 40 wt %. In a particularly preferred embodiment, in combination with any of the embodiments listed below or above, the dry matter content of gum arabic in the solution is 20 to 30 wt %.

The term "dry matter" is directed to gum arabic that has been dried in the course of its processing upon harvest. The dry matter can be derived from the native, raw, untreated gum arabic, which is merely crushed into granules, or from further processed and purified gum arabic wherein the processing of the raw gum arabic comprises the steps of crushing the raw, hard gum arabic into pieces, dissolving them in water, filtering, pasteurizing and drying, which is preferably performed as spray drying.

The residual moisture content of the raw, unprocessed gum arabic dry matter depends on the commercial source wherefrom the gum arabic is purchased, and is preferably below 15 wt %. The residual moisture content of the processed and spray-dried gum arabic also depends on the commercial source, and is preferably below 10 wt %.

Duration of the enzymatic treatment according to the invention should be adjusted in combination with temperature and pH-value. In a preferred embodiment of the invention, in combination with any of the embodiments above and below, the gum arabic is treated for 2 to 100 h with the enzyme selected from the group of glycosidases. In a more preferred embodiment, in combination with any of the embodiments listed below or above, the gum arabic is treated for 24 to 72 h. In a particularly preferred embodiment, in combination with any of the embodiments listed below or above, the gum arabic is treated for 40 to 50 h.

As for the pH, it is a preferred embodiment of the invention, in combination with any of the embodiments above or below, to treat the gum arabic at a pH being in the range of from 2 to 9 in the method according to the invention. In a more preferred embodiment, in combination with any of the embodiments listed below or above, the gum arabic is treated at a pH ranging from 3 to 7. In a particularly preferred embodiment, in combination with any of the embodiments listed below or above, the gum arabic is treated at a pH in the range of 4 to 5.

Regarding the combination of process parameters, it is a preferred embodiment, in combination with any of the embodiments listed above or below, to carry out the enzymatic treatment of gum arabic according to the method of the invention at a temperature of 40 to 60° C. for 5 to 60 h, at a pH of the solution being in the range from 2 to 9. In a more preferred embodiment, in combination with any of the embodiments listed above or below, the enzymatic treatment is carried out at 45 to 55° C. for 24 to 48 h at a pH of 4 to 5. In a particularly preferred embodiment, in combination with any of the embodiments listed above or below, the enzymatic treatment of gum arabic according to the method of the invention is carried out at 50° C. at a pH of 4.4 for 45 h.

Optimum incubation conditions for a certain process can be identified by an increase in the amount of enzymatically cleaved galactose, expressed as free galactose content when using β-galactosidase as the enzyme selected from the group of glycosidases. Based on a 20 wt % gum arabic solution, the final amount of released galactose during the process is preferably 20 and 1000 mg/kg gum arabic solution, more preferably between 50 and 500 mg/kg gum arabic solution and particularly preferably between 100 and 200 mg/kg gum arabic solution.

The method according to the invention is suitable for obtaining a modified gum arabic having improved emulsifying properties, which is suitable for being used as an emulsifier, meaning a substance that stabilizes an emulsion by increasing its kinetic stability.

The modified gum arabic according to the invention can be used for the production of an emulsion. The emulsion comprising the modified gum arabic obtainable by the method according to the invention represents, in combination with any other embodiments listed above or below, a further embodiment of the invention.

The term "emulsion" as used herein relates to a mixture of two or more liquids being normally immiscible. In a preferred embodiment of the present invention, the emulsion comprising the modified gum arabic obtainable by the method in accordance to the invention, is an oil-in-water emulsion. The emulsion can be produced by standard procedures known to the person skilled in the art, e.g. by means of homogenisation with high-pressure homogenizers, microfluidizers, rotor-stator-systems, membrane homogenizers and ultrasonic homogenizers. In a preferred embodiment, in combination with any of the embodiments listed above or below, the emulsion is produced by means of a high pressure homogenizer.

The emulsion can be used as an additive in ready-to-drink beverages so as to achieve a cloudy beverage. The emulsion can also be mixed with other ingredients in order to obtain a raw material (concentrate) for the production of a ready-to-drink beverage, which is achieved by the dilution of the concentrate with water and the addition of other components like, for example, sugar and acid. The emulsion may be added to the beverage in an amount of 0.05 to 0.3 wt %, based on the total weight of the beverage. Furthermore, to obtain a colored cloudy drink, a fat-soluble colorant, such as a carotinoid, may be added to the oil phase of the emulsion.

A further embodiment of the invention, combinable with any of the embodiments listed above or below, therefore is a beverage concentrate comprising the above emulsion in accordance with the invention. Beverage concentrates comprise, for example, energy drink concentrates, soft drink concentrates, coke drink concentrates, and juice drink concentrates.

Another embodiment, combinable with any of the embodiments listed above or below, is a ready-to-drink beverage comprising the above emulsion according to the invention. Ready-to-drink beverages comprise, for example, energy drinks, soft drinks, coke drinks, and juice drinks.

EXAMPLES

The following examples describe the invention.

All concentrations are given in wt %, unless stated otherwise.

Example 1: Release of Galactose from Gum Arabic Molecules by Means of Lactase Enzyme A 20 wt % aqueous solution of gum arabic was prepared by dissolving dried gum arabic powder (commercial sample of *Acacia senegal* var. *Senegal*, purchased from Alland & Brand) at room temperature for about 1 h. The pH value of the gum arabic solution was ~pH 4.4, which is near the range for optimum enzyme activity. Hence, no adjustment of the pH was made. The solution was then split into three equal parts, heated up to 50° C. in a water bath and the respective amount (100 ppm/500 ppm/1000 ppm [=27.7/138.5/277 units/g gum arabic]) of lactase enzyme (Biocatalysts Lactase L017P with an activity of 65,000 lactase units/gram) was added to each part. After various times, aliquots were removed, the enzyme was inactivated by means of heating the gum arabic solution (85° C./10 min), and the amount of free galactose was analytically detected.

FIG. 1 shows the increase of free galactose in dependency of incubation time and enzyme concentration. The results demonstrate that in general, only a very small amount of galactose is released, compared to the total dry matter in the system. Even in the case of the most intense treatment (1000 ppm for 45 h), about 450 mg of galactose is released from 1 kg of 20 wt % gum arabic solution. Hence, less then 1 wt % of the available gum arabic dry matter is hydrolyzed in this case.

Example 2: Change of HPLC Pattern

Each sample from example 1 was analyzed by means of HPLC-UV detection. FIGS. 2a and 2b show the change in the chromatographic pattern due to enzymatic treatment with 100 ppm for 45 h at 50° C. As can be taken from FIG. 2b, there is a significant change, although only about 100 mg of galactose is released from 1 kg of 20 wt % gum arabic solution (see example 1). Samples that were stored under process conditions (50° C./40 h) without enzyme addition did not show any significant chance of HPLC-pattern (not shown). Hence, the change is solely caused by the enzymatic reaction.

Example 3: Preparation of Emulsions From Commercial Gum Arabic Powder Samples Four different commercial dry powder gum arabic samples derived from *Acacia senegal* var. *senegal* (purchased from ISC Europe, Norevo, Alland & Robert) were tested regarding the change in emulsifying properties due to enzymatic treatment.

23.5 wt % aqueous solutions of gum arabic were prepared by dissolving gum arabic powder at room temperature for about 1 h. The solutions were then heated to 50° C. in a water bath and respectively incubated with 100 ppm (27.7 units/g gum arabic) of lactase enzyme (Biocatalysts Lactase L017P with an activity of 65,000 lactase units/gram). After incubation for 45 h at 50° C., the samples were cooled to room temperature (25° C.) and immediately used for the emulsifying experiments. For comparison, samples without added enzyme were equally treated and stored for 45 h at 50° C. before the emulsions were prepared.

For the preparation of the emulsions, 85.04 g gum arabic solution was mixed with 14.2 g of oil-phase (51.12 wt % ester gum, 48.74 wt % orange oil terpenes and 0.14 wt % antioxidants) and 0.76 g of a 50 wt % aqueous solution of citric acid, and emulsified at room temperature by means of an ultra-turrax for 5 minutes.

FIG. 3a shows the volume-weighted particle size ($X_{90,3}$) for the emulsions with and without enzymatic treatment directly after preparation. Subsequently, the emulsions were heated (90° C. for 20 min) as a stress test, and the particle size distribution was measured for a second time.

$X_{90,3}$ is the measured value in µm from which droplets representing 90% of the disperse phase volume of an emulsion sample have a smaller diameter. The particle size was measured by means of a Sympatec GmbH HELOS BR with the standard laser diffraction method.

FIG. 3b shows the increase in particle size ($X_{90,3}$; µm) that was found due to the heat treatment. The heat-treated samples did not show any further significant changes in particle sizes after 4 weeks of storage at room temperature, regardless enzymatic treatment or not (results not shown). As can be taken from the results shown in FIGS. 3a and 3b, the emulsions from enzymatically treated gum arabic solutions generate significantly smaller oil droplets and are more stable after heat treatment compared to emulsions from non-enzyme treated gum arabic solutions.

Example 4: Influence of Enzyme Concentration and Incubation Temperature

A commercial, dry powder gum arabic sample derived from *Acacia senegal* var. *Senegal* (purchased from Alland & Robert) was treated according to example 3 with the exception that the incubation temperatures as well as the enzyme concentrations were varied. The emulsions were prepared according to example 3 and the particle size distributions were measured without pre-heat treatment.

FIGS. 4a and 4b show the volume-weighted particle sizes ($X_{90,3}$; µm) for the emulsions directly after preparation for differently treated samples. As can be taken from FIGS. 4a and 4b, the effect of enzyme treatment on the resulting emulsion particle sizes strongly depends on the reaction intensity, caused by the selected incubation conditions.

Example 5: Preparation of Emulsions From Unprocessed, Native Gum Arabic Samples (Granules)

A commercial sample (purchased from Norevo) of unprocessed, native gum arabic granules (~0.5 cm diameter) derived from *Acacia senegal* var. *senegal* was used for the preparation of a 23.5 wt % aqueous gum arabic solution. In this case, the granules were dissolved in water at room temperature for 1.5 h and subsequently filtered trough a 200 µm sieve to remove external particles. The gum arabic solution was treated according to example 3 to create emulsions, with the difference that the native gum arabic solutions were pasteurized (80° C./30 min) after the incubation time of 45 h at 50° C., regardless an enzymatic treatment or none.

FIG. 5 shows the volume-weighted particle size ($X_{90,3}$; µm) for the emulsions with and without enzymatic treatment directly after preparation and after heating for 20 min at 90° C., respectively. As can be taken from FIG. 5, a positive effect of an enzymatic treatment, expressed as smaller emulsion oil droplets, can also be achieved when native, unprocessed gum arabic samples are used as a substrate.

Example 6: Preparation of Emulsions from Unprocessed, Native Gum Arabic Samples (Granulate), Treatment with High-Pressure Homogenizer A commercial sample (purchased from Norevo) of unprocessed, native gum arabic granules (~0.5 cm diameter) derived from *Acacia senegal* var. *senegal* was used to prepare a 23.5 wt % aqueous gum arabic solution. The granules were dissolved in water at room temperature for 1.5 h and subsequently filtered through a 200 μm sieve to remove external particles. The solution was then split into two parts. One half of the solution was heated up to 50° C. in a water bath and incubated with 100 ppm (27.7 units/g of gum arabic) of lactase enzyme (Biocatalysts Lactase L017P with an activity of 65.000 lactase units/gram) for 45 h and subsequently used for the preparation of an emulsion without any pasteurisation step. As a comparison, the other half of the sample was directly used for the preparation of emulsions, without any enzymatic treatment.

For the preparation of the emulsions, 85.04 wt % of the respective gum arabic solution was mixed with 14.2 wt % of the oil-phase (51.12 wt % ester gum, 48.74 wt % orange oil terpenes and 0.14 wt % antioxidants) and 0.76% of a 50 wt % aqueous solution of citric acid, and pre-emulsified at room temperature by means of an ultra-turrax for 7 minutes. Subsequently, the emulsions were further emulsified by means of a high-pressure homogenizer for two passes at 200 bar with a volumetric flow of 12 L/h.

As a stress test, an aliquot from both emulsions was heated (90° C. for 20 min). The particle size distribution was measured after the high pressure homogenization and the heat treatment, respectively.

FIG. 6 shows the volume-weighted particle size ($X_{90,3}$; μm) for the emulsions with and without enzymatic treatment directly after preparation by means of high pressure homogenization and after heating of the emulsion for 20 min at 90° C., respectively. As can be taken from FIG. 6, a positive effect of an enzymatic treatment, expressed as smaller emulsion oil droplets, can be achieved by using high-pressure homogenization technology for the preparation of the emulsion. A possible increase of emulsifying properties of gum arabic due to enzymatic treatment is generally independent from the applied homogenization device. It can also be seen that the stability of the emulsion during a high-heating stress test is increased due to enzymatic treatment. From examples 5 and 6, it can further be concluded that an optional pasteurisation step can generally be incorporated into the process at any desired point.

The invention claimed is:

1. A method for preparing modified gum arabic comprising treating gum arabic with an enzyme at a concentration of 10 to 1000 units of enzyme per gram of gum arabic at a temperature of 40° C. to 60° C., wherein 0.01 to 0.3% of galactose is removed from the gum arabic based on applied gum arabic mass, wherein the enzyme is β-galactosidase and the gum arabic is a solution with a dry matter content of 20 to 30 wt % based on the total weight of the solution.

2. The method according to claim 1, wherein the concentration is 10 to 500 units of the enzyme per gram of gum arabic.

3. The method according to claim 2, wherein the concentration is 25 to 250 units of the enzyme per gram of gum arabic.

4. The method according to claim 1, wherein the gum arabic is treated for 5 to 60 h.

5. The method according to claim 1, wherein the gum arabic is treated at a pH in the range of from 2 to 9.

6. Modified gum arabic produced by the method according to claim 1.

7. Emulsion comprising the modified gum arabic according to claim 6.

8. The emulsion according to claim 7, wherein the emulsion is an oil-in-water emulsion.

9. Beverage concentrate comprising the emulsion according to claim 7.

10. Ready-to-drink beverage comprising the emulsion according to claim 7.

* * * * *